United States Patent
Torii et al.

(10) Patent No.: US 8,045,150 B2
(45) Date of Patent: Oct. 25, 2011

(54) SEMICONDUCTOR WAFER INSPECTION METHOD

(75) Inventors: Kantarou Torii, Nagasaki (JP); Kouichi Imura, Nagasaki (JP)

(73) Assignee: Sumco Techxiv Corporation, Nagasaki (JP)

( * ) Notice: Subject to any disclaimer, the term of this patent is extended or adjusted under 35 U.S.C. 154(b) by 195 days.

(21) Appl. No.: 12/555,170

(22) Filed: Sep. 8, 2009

(65) Prior Publication Data

US 2010/0060891 A1  Mar. 11, 2010

(30) Foreign Application Priority Data

Sep. 11, 2008  (JP) ................................. 2008-233937

(51) Int. Cl.
*G01N 21/00* (2006.01)
(52) U.S. Cl. ................... 356/237.5; 356/237.2
(58) Field of Classification Search .... 356/237.1–237.6; 382/145–152
See application file for complete search history.

(56) References Cited

U.S. PATENT DOCUMENTS

2003/0169916 A1  9/2003  Hayashi et al.
2009/0147250 A1  6/2009  Tanaka et al.

FOREIGN PATENT DOCUMENTS

JP  2003-139523  5/2003
JP  2003-243465  8/2003

OTHER PUBLICATIONS

English language Abstract of JP 2003-139523, May 14, 2003.
English language Abstract of JP 2003-243465, Aug. 29, 2003.

*Primary Examiner* — Gregory J. Toatley, Jr.
*Assistant Examiner* — Tri T Ton
(74) *Attorney, Agent, or Firm* — Greenblum & Bernstein P.L.C.

(57) ABSTRACT

A semiconductor wafer inspection method includes: an imaging step in which a first image being an image of the chamfered surface seen from the main surface side and a second image being an image of the chamfered surface seen from the back surface side are taken; a calculation step in which a first width is obtained based on the first image, the first width being a width of the chamfered surface seen from the main surface side, a second width is obtained based on the second image, the second width being a width of the chamfered surface seen from the back surface side, and a ratio of the first width to the second width thus obtained is calculated; and a shape determination step in which a form of the chamfered surface is determined to be abnormal in a case where the ratio is out of a predetermined range.

4 Claims, 7 Drawing Sheets

SEMICONDUCTOR WAFER INSPECTION METHOD

This application is based on and claims the benefit of priority from Japanese Patent Application No. 2008-233937, filed on 11 Sep. 2008, the content of which is incorporated herein by reference.

BACKGROUND OF THE INVENTION

1. Field of the Invention

The present invention relates to a semiconductor wafer inspection method.

2. Related Art

A semiconductor wafer often includes a principal surface that is a planar surface and a chamfered surface that is formed in a peripheral portion. The chamfered portion is chamfered and thus can prevent damage of the semiconductor wafer in a case where an external force is applied to the peripheral portion.

A defect such as a crack, a projection, an attached particle and the like that is present on the chamfered surface increases the likelihood of cracking, breakage and the like of the semiconductor wafer during processing of the semiconductor wafer.

In order to detect such a defect of a chamfered surface, a technique for taking images of a chamfered surface from a plurality of positions and detecting a defect of the chamfered surface based on a plurality of images thus taken is proposed (for example, see Japanese Unexamined Patent Applications Publication Nos. 2003-139523 and 2003-243465).

Here, in an inspection of a chamfered surface, in addition to detection of a defect, determination of whether or not a chamfered surface shape is abnormal is required. However, in the technique disclosed in Japanese Unexamined Patent Applications Publication Nos. 2003-139523 and 2003-243465, though a defect of the chamfered surface can be detected, it cannot be determined whether or not the shape of the chamfered surface is abnormal. As a result, a separate step of determination of whether or not the shape of the chamfered portion is abnormal is required, and thus there has been a problem in throughput of inspection processing being decreased.

SUMMARY OF THE INVENTION

Given this, the present invention aims at providing a semiconductor wafer inspection method that facilitates determination of whether or not the shape of the chamfered portion is abnormal.

A semiconductor wafer inspection method according to the present invention is a semiconductor wafer inspection method that inspects a chamfered surface provided on a main surface, a back surface, and a peripheral portion of a semiconductor wafer, comprising: an imaging step in which a first image is taken using a first imaging device, the first image being an image of the chamfered surface seen from the main surface side and a second image is taken using a second imaging device, the second image being an image of the chamfered surface seen from the back surface side; a calculation step in which a first width is obtained based on the first image taken in the imaging step, the first width being a width of the chamfered surface seen from the main surface side, a second width is obtained based on the second image taken in the imaging step, the second width being a width of the chamfered surface seen from the back surface side, and a ratio of the first width to the second width thus obtained is calculated; and a shape determination step in which a form of the chamfered surface is determined to be abnormal in a case where the ratio calculated in the calculation step is out of a predetermined range.

In addition, the first imaging device and the second imaging device are preferably disposed to be line-symmetrical across a plane equally dividing the semiconductor wafer in a thickness direction.

Furthermore, a defect detection step in which a defect of the chamfered surface is detected based on the first image and the second image taken in the imaging step is preferably further included.

Moreover, in the imaging step, a third image is preferably further taken using a third imaging device, the third image being an image of the chamfered surface that is seen to the inside of the semiconductor wafer in a radial direction, and, in the defect detection step, a defect of the chamfered surface is preferably detected based on the first image, the second image and the third image.

According to the present invention, a semiconductor wafer inspection method that facilitates determination of whether or not the shape of the chamfered portion is abnormal can be provided.

DETAILED DESCRIPTION OF THE INVENTION

First Embodiment

A first embodiment of the semiconductor wafer inspection method according to the present invention is hereinafter described with reference to the drawings. First, an inspection device 1 used in the first embodiment of the semiconductor wafer inspection method according to the present invention is described.

Figure 1:
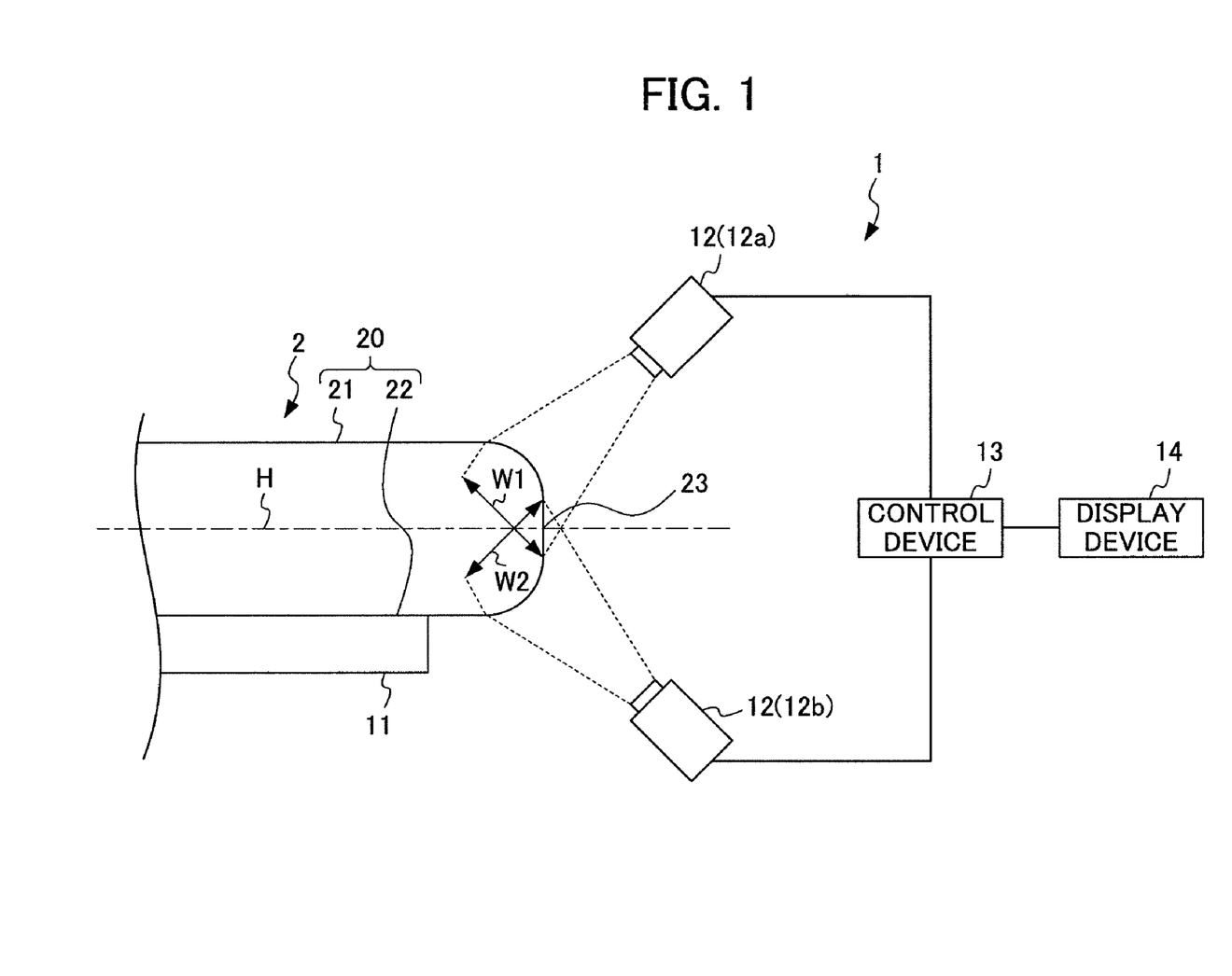
FIG. 1 is a side view schematically showing an inspection device 1 and a semiconductor wafer 2 used in an inspection method according to a first embodiment.

FIG. 1 is a side view schematically showing an inspection device 1 and a semiconductor wafer 2 used in an inspection method according to a first embodiment.

First, the semiconductor wafer 2 in which a chamfered surface 23 is formed in a peripheral portion thereof is described with reference to FIG. 1. The semiconductor wafer 2 according to the first embodiment is, for example, a silicon wafer or a gallium arsenide wafer.

As shown in FIG. 1, an external aspect (surface) of the semiconductor wafer 2 includes a principal surface 20 that is a planar surface and a chamfered surface 23 that is formed in a peripheral portion.

The principal surface 20 includes a main surface 21 on which a semiconductor device is formed and a back surface 22 that is an opposite surface to the main surface 21.

Next, the inspection device 1 used in the semiconductor wafer inspection method according to the first embodiment is described. The inspection device 1 of the first embodiment is a device that detects a defect of the chamfered surface 23 of the semiconductor wafer 2 and determines whether or not the shape of the chamfered surface 23 is abnormal.

As shown in FIG. 1, the inspection device 1 includes a rotating table 11, an imaging device 12 (12a and 12b), a control device 13, and a display device 14.

The rotating table 11 can mount the semiconductor wafer 2 thereon and hold the semiconductor wafer 2 thus mounted. The rotating table 11 is configured to rotate about a rotational axis that passes through the center of the rotating table 11 and extends in a thickness direction of the rotating table 11.

The imaging device 12 is composed of, for example, a CCD camera. The imaging device 12 includes a first imaging device 12a and a second imaging device 12b. The first imaging device 12a is disposed at a position that faces the chamfered surface 23 seen from the main surface 21 side.

The first imaging device 12a takes an image of the chamfered surface 23 on the main surface 21 side. The second imaging device 12b is disposed at a position that faces the chamfered surface 23 seen from the back surface 22 side. The second imaging device 12b takes an image of the chamfered surface 23 on the back surface 22 side.

The first imaging device 12a and the second imaging device 12b are disposed to be line-symmetrical across a plane H equally dividing the semiconductor wafer 2 in a thickness direction. As a result, the first imaging device 12a and the second imaging device 12b can take an image of the entire chamfered surface 23.

Behavior of the imaging device 12 is hereinafter described.

First, the rotating table 11 on which the semiconductor wafer 2 is mounted rotates at a constant rate. The imaging device 12 takes an image of the chamfered surface 23 so that imaging ranges, in a case where the semiconductor wafer 2 is seen in planar view, are each a predetermined angle from a center of the semiconductor wafer 2. The predetermined angle is preferably 10 to 30°. The imaging device 12 thus can take an image of the entire chamfered surface 23.

The control device 13 is connected with the imaging device 12 and the display device 14. The control device 13 controls the imaging device 12 and the display device 14. The control device 13 detects a defect of the chamfered surface 23 based on the image taken by the imaging device 12. In addition, the control device 13 determines whether or not the shape of the chamfered surface 23 is abnormal, based on the image taken by the imaging device 12. Detection of a defect of the chamfered surface 23 and determination of whether or not the shape is abnormal are described later in detail.

The display device 14 is composed of an LCD (liquid crystal display) or the like. The display device 14 is connected with the control device 13. The display device 14 displays a defect of the chamfered surface 23 detected by the control device 13 and a result of determination of the shape.

Figure 2:
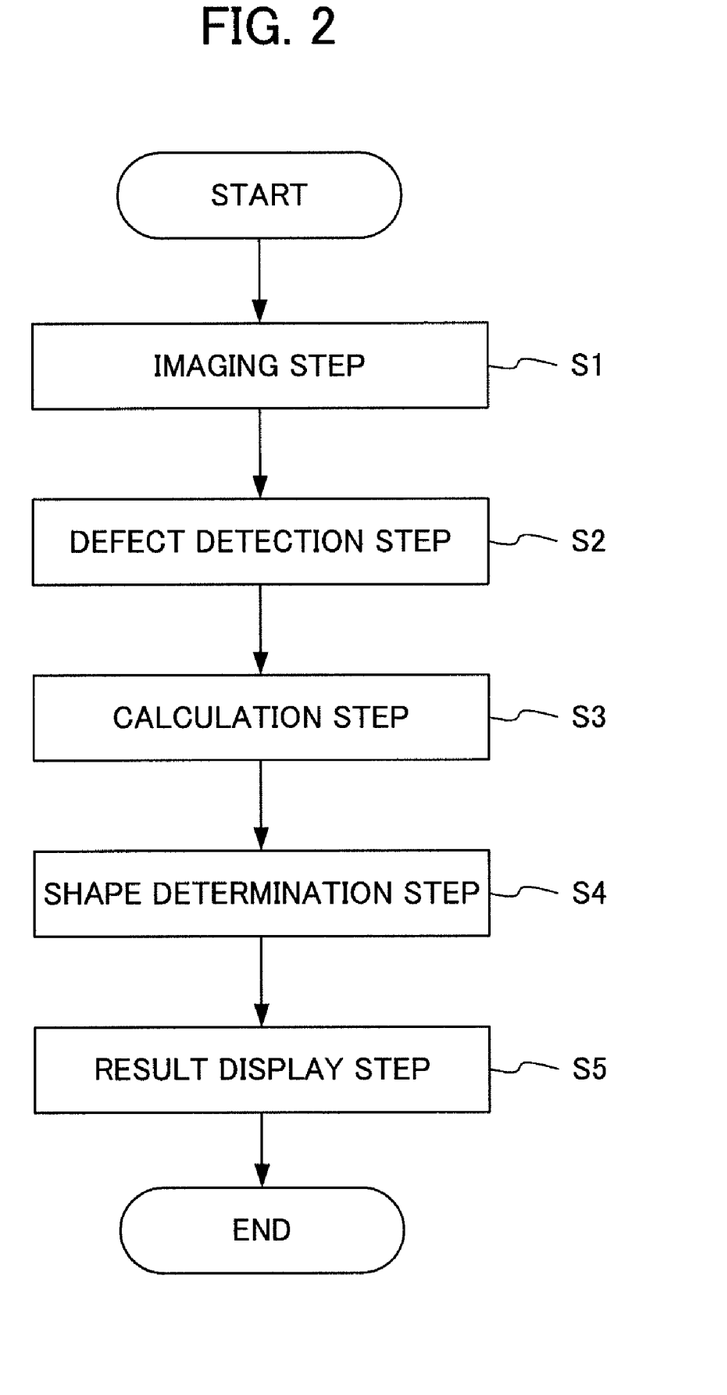
FIG. 2 is a flow chart showing the semiconductor wafer inspection method according to the first embodiment.

FIG. 2 is a flow chart showing the semiconductor wafer inspection method according to the first embodiment. The semiconductor wafer inspection method of the first embodiment includes an imaging step S1, a defect detection step S2, a calculation step S3, a shape determination step S4 and a result display step S5. Each step is described hereinafter. In the semiconductor wafer inspection method of the first embodiment, the inspection is performed using the above-mentioned inspection device 1.

(S1) Imaging Step

First, in the imaging step S1, the inspection device 1 takes a first image using the first imaging device 12a, the first image being an image of the chamfered surface 23 seen from the main surface 21 side. In addition, the inspection device 1 takes a second image using the second imaging device 12b, the second image being an image of the chamfered surface 23 seen from the back surface 22 side.

The first image and the second image thus taken include the entire chamfered surface 23.

(S2) Defect Detection Step

After the imaging step S1, the control device 13 detects a defect of the chamfered surface 23 based on the first image and the second image taken in the imaging step S1. More specifically, the control device 13 performs a predetermined process on the first image and the second image, thus detecting a defect of the chamfered surface 23. As the predetermined process, a process of determining a region which has brightness exceeding a certain range compared to reference brightness, as a defect, regarding each of the first image and the second image, may be cited. The defect of the chamfered surface 23 includes a crack, a projection, an attached particle and the like.

(S3) Calculation Step

After the defect detection step S2, the control device 13 obtains a first width W1, which is a width of the chamfered surface 23 seen from the main surface 21 side (see FIG. 1), based on the first image taken in the imaging step S1. In addition, the control device 13 obtains a second width W2, which is a width of the chamfered surface 23 seen from the back surface 22 side (see FIG. 1), based on the first image taken in the imaging step S1. Thereafter, the control device 13 calculates a ratio P of the first width W1 to the second width W2 thus obtained (W1/W2 or W2/W1).

(S4) Shape Determination Step

After the calculation step S3, the control device 13 determines a form of the chamfered surface 23 to be abnormal in a case where the ratio P calculated in the calculation step S3 is out of a predetermined range. Here, the predetermined range is a range of the ratio P of the first width W1 to the second width W2 in a case where the chamfered surface 23 has a shape within a standard. More specifically, the predetermined range is a range of the ratio P of the first width W1 to the second width W2 calculated in the calculation step S3 that is acceptable in a case where the chamfered surface 23 has a shape within a standard.

(S5) Result Display Step

After the shape determination step S4, the control device 13 displays on the display device 14 a defect of the semiconductor wafer 2 detected in the defect detection step S2 and the shape of the chamfered surface 23 determined to be abnormal in the shape determination step S4.

As described above, in the calculation step S3, the semiconductor wafer inspection method of the first embodiment obtains the first width W1, which is a width of the chamfered surface 23 seen from the main surface 21 side, based on the first image. In addition, in the calculation step S3, the semiconductor wafer inspection method of the first embodiment obtains the second width W2, which is a width of the chamfered surface 23 seen from the back surface 22 side, based on the second image. Furthermore, in the calculation step S3, the semiconductor wafer inspection method of the first embodiment calculates the ratio P of the first width W1 to the second width W2 thus obtained. In the shape determination step S4, a form of the chamfered surface 23 is determined to be abnormal in a case where the ratio P calculated in the calculation step S3 is out of a predetermined range.

As described above, the semiconductor wafer inspection method of the first embodiment can detect a defect of the chamfered surface 23 and determine whether or not the shape of the chamfered surface 23 is abnormal. Since the semiconductor wafer inspection method of the first embodiment can detect a defect of the chamfered surface 23 and determine whether or not the shape of the chamfered surface 23 is abnormal at the same time, throughput of inspection processing can be improved.

In addition, the semiconductor wafer inspection method of the first embodiment can be easily performed in a final inspection step in a process of manufacturing the semiconductor wafer 2. Therefore, the semiconductor wafer inspection method of the first embodiment can determine the shape of the chamfered surface 23 without affecting quality of the semiconductor wafer 2. As a result, according to the semiconductor wafer inspection method of the first embodiment, all of the semiconductor wafers 2 subjected to an inspection can easily inspected. Hence, the semiconductor wafer inspection method of the first embodiment can improve inspection accuracy of determination of the shape of the chamfered surface 23.

Second Embodiment

Next, a second embodiment of the semiconductor wafer inspection method according to the present invention is hereinafter described with reference to the drawings. Regarding a semiconductor wafer inspection method of the second embodiment, a description centered on differences from the semiconductor wafer inspection method of the first embodiment is given hereinafter, and a description for other elements is omitted.

Figure 3:
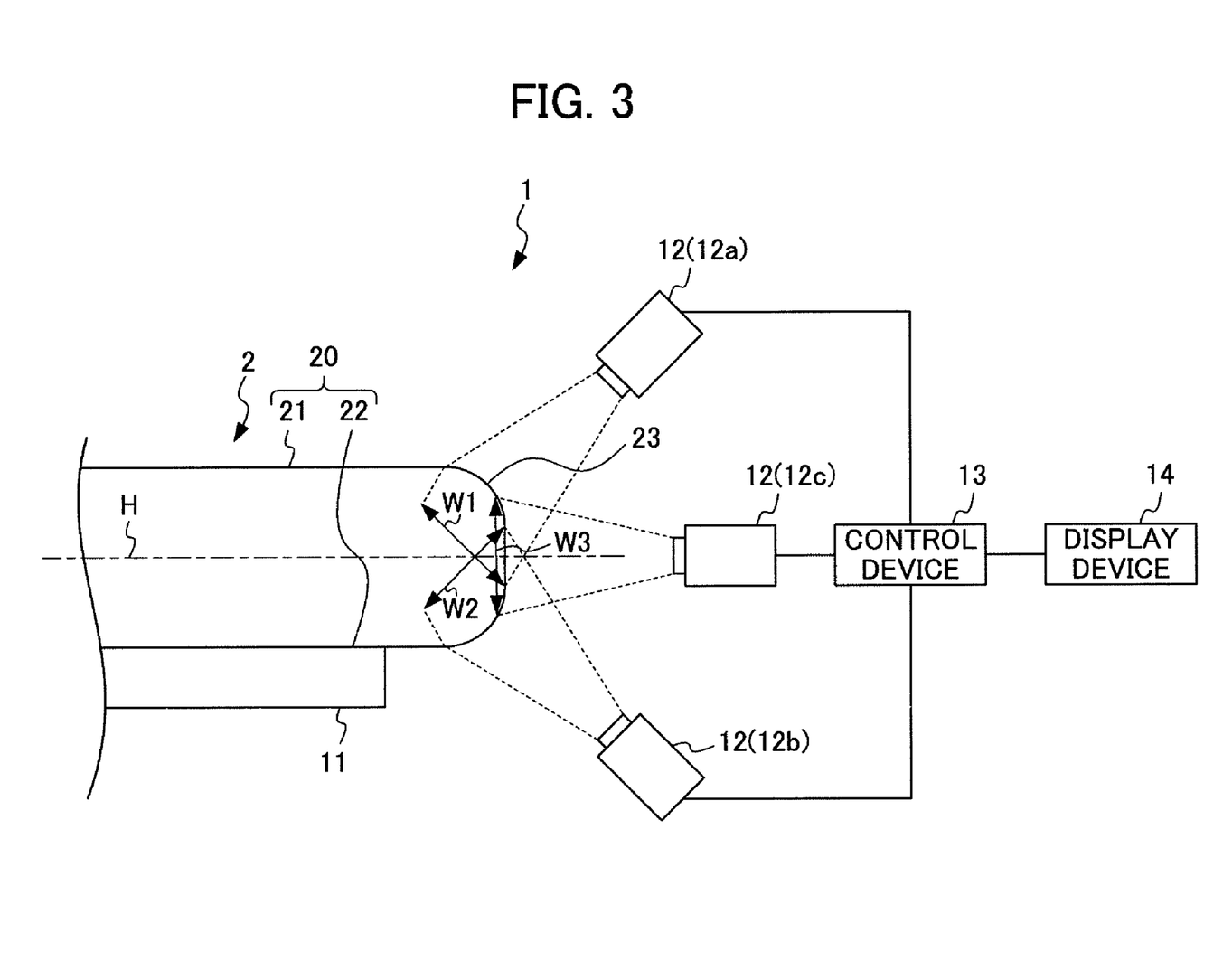
FIG. 3 is a side view schematically showing an inspection device 1 and a semiconductor wafer 2 used in an inspection method according to a second embodiment.

FIG. 3 is a side view schematically showing an inspection device 1 and a semiconductor wafer 2 used in an inspection method according to a second embodiment. The second embodiment is different from the first embodiment mainly in that a third imaging device 12c is used in addition to the first imaging device 12a and the second imaging device 12b, in other words that three imaging devices are used.

As shown in FIG. 3, the third imaging device 12c is disposed at a position that faces the chamfered surface 23 that is seen to the inside of the semiconductor wafer 2 in a radial direction. The third imaging device 12c takes an image of the chamfered surface 23. A third width W3 (see FIG. 3) is a width of the chamfered surface 23 that is seen to the inside of the semiconductor wafer 2 in a radial direction.

Figure 4:
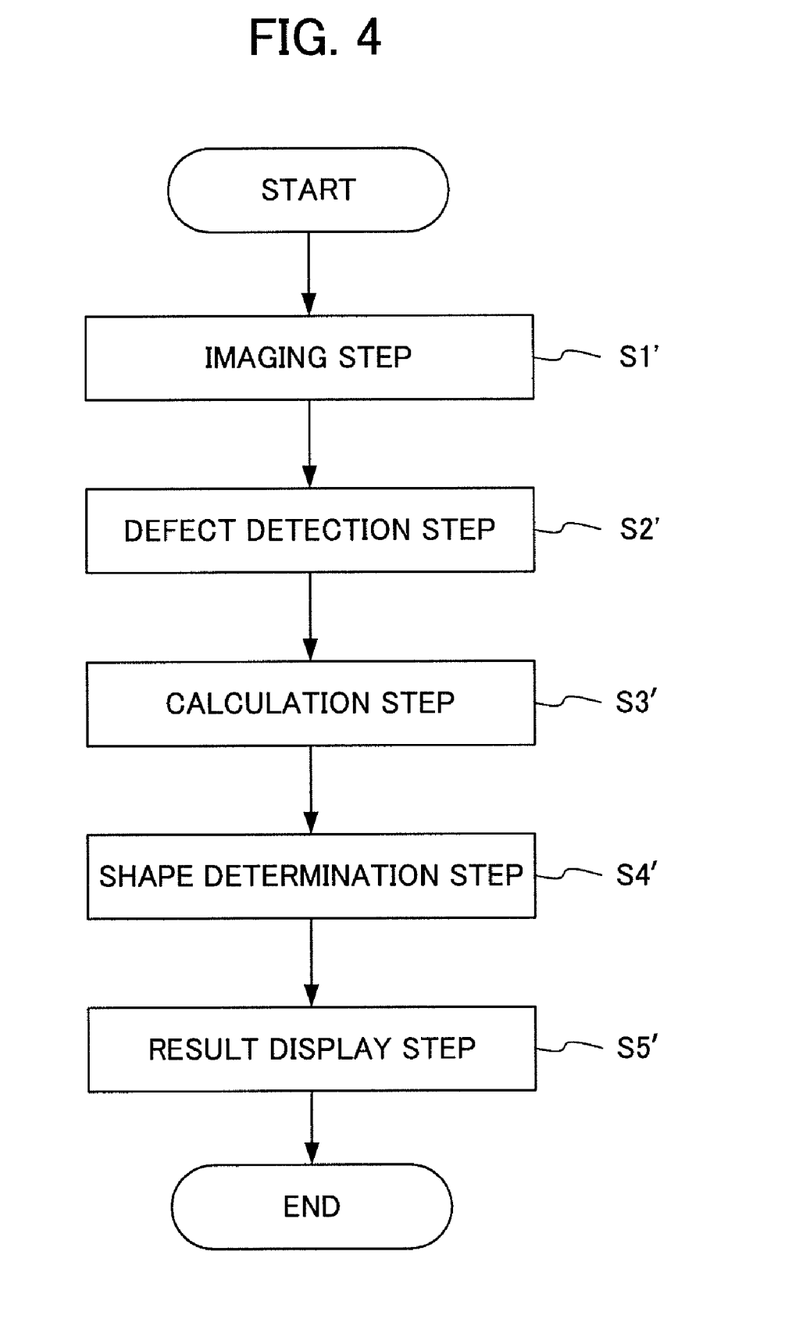
FIG. 4 is a flow chart showing the semiconductor wafer inspection method according to the second embodiment.

FIG. 4 is a flow chart showing the semiconductor wafer inspection method according to the second embodiment. The semiconductor wafer inspection method of the second embodiment includes an imaging step S1', a defect detection step S2', a calculation step S3', a shape determination step S4', and a result display step S5' described later. Each step is described hereinafter. It should be noted that the steps S3' to S5' are similar to the steps S3 to S5 in the first embodiment and therefore a description thereof is omitted.

(S1') Imaging Step

The inspection device 1 takes a first image using the first imaging device 12a, the first image being an image of the chamfered surface 23 seen from the main surface 21 side. In addition, the inspection device 1 takes a second image using the second imaging device 12b, the second image being an image of the chamfered surface 23 seen from the back surface 22 side. In addition, the inspection device 1 takes a third image using a third imaging device 12c, the third image being an image of the chamfered surface 23 that is seen to the inside of the semiconductor wafer 2 in a radial direction. The first image, the second image and the third image thus taken include the entire chamfered surface 23.

(S2') Defect Detection Step

After the imaging step S1', the control device 13 detects a defect of the chamfered surface 23 based on the first image, the second image and the third image taken in the imaging step S1'.

According to the semiconductor wafer inspection method of the second embodiment, the following effect can be obtained in addition to the effect of the first embodiment. That is, in the semiconductor wafer inspection method of the second embodiment, the third image is taken using the third imaging device 12c. In addition, in the semiconductor wafer inspection method of the second embodiment, a defect of the chamfered surface 23 is detected based on the first image, the second image and the third image. Hence, the semiconductor wafer inspection method of the second embodiment can increase the amount of information of each image, and thus can improve inspection accuracy of detection of a defect of the chamfered surface 23.

An embodiment of the present invention has been described above; however, the present invention is not limited thereto. For example, although two or three imaging devices 12 are used in the abovementioned first and second embodiments, the present invention is not limited thereto. In the present invention, the number of imaging devices 12 can be increased for taking an image of the chamfered surface 23.

EXAMPLES

Next, the present invention is described in more detail using examples. It should be noted that the examples are not intended to limit the scope of the present invention.

Imaging Step According to First Embodiment

Figure 5:
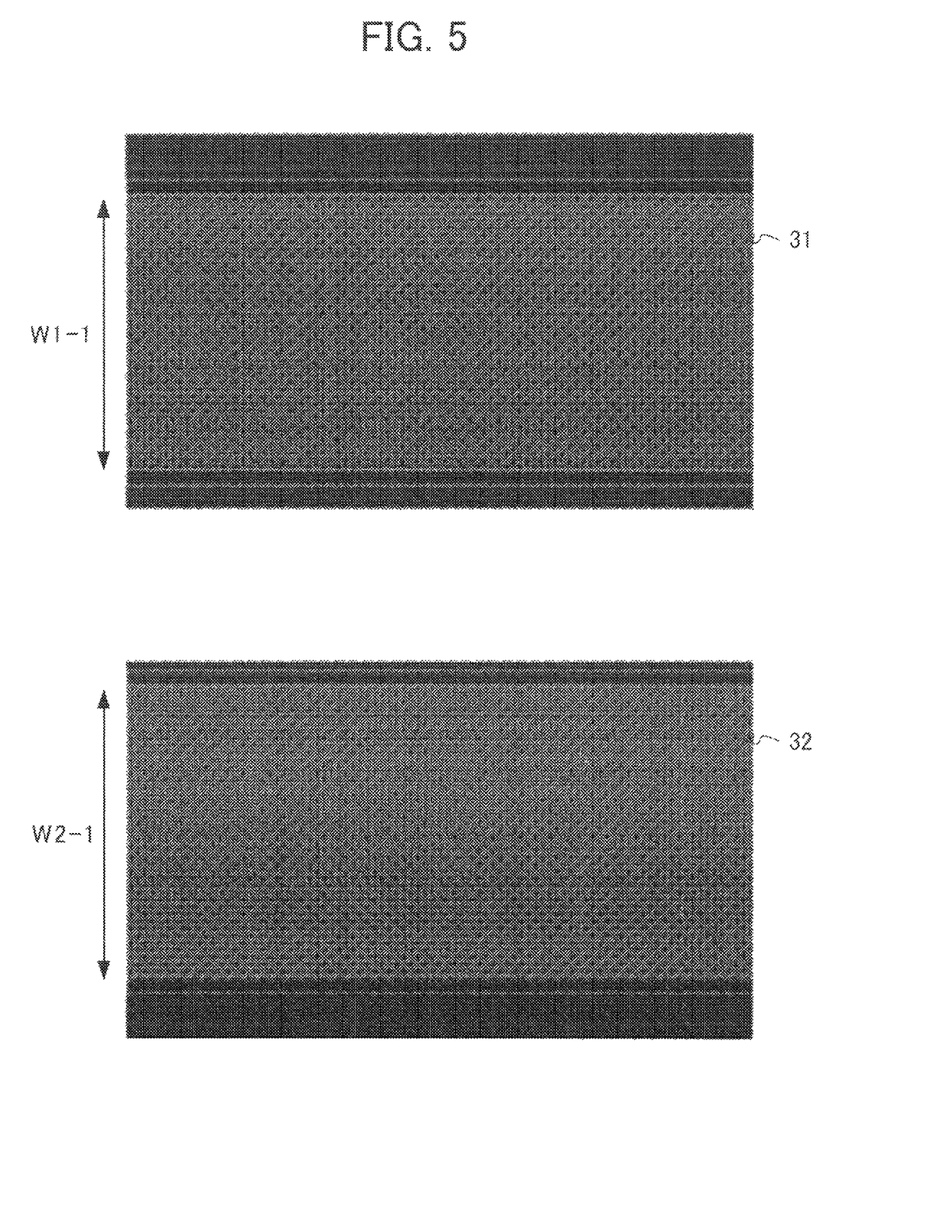
FIG. 5 is an image of a chamfered surface of a semiconductor wafer taken by an imaging device corresponding to the first embodiment.

An inspection device that performs the semiconductor wafer inspection method according to the present invention includes two or three imaging devices. As the inspection device that performs the semiconductor wafer inspection method according to the present invention, Edgescan manufactured by Raytex Corporation and an edge inspection device manufactured by Nippon Electro-Sensory Devices (NED) Co., Ltd. were used. An image of a chamfered surface of a semiconductor wafer was taken by two imaging devices and images shown in FIG. 5 were obtained. FIG. 5 shows images of a chamfered surface of a semiconductor wafer taken by imaging devices. As shown in FIG. 5, an image 31 is an image of a chamfered surface seen from a main surface side. An image 32 is an image of a chamfered surface seen from a back surface side. A width W1-1 of the chamfered surface in the image 31 is the width of the chamfered surface seen from the main surface side (a first width). A width W2-1 of the chamfered surface in the image 32 is the width of the chamfered surface seen from the back surface side (a second width).

Obtaining the widths W1-1 and W2-1 of the chamfered surface using the images 31 and 32 taken by the imaging devices was thus confirmed to be possible.

Imaging Step According to Second Embodiment

Figure 6:
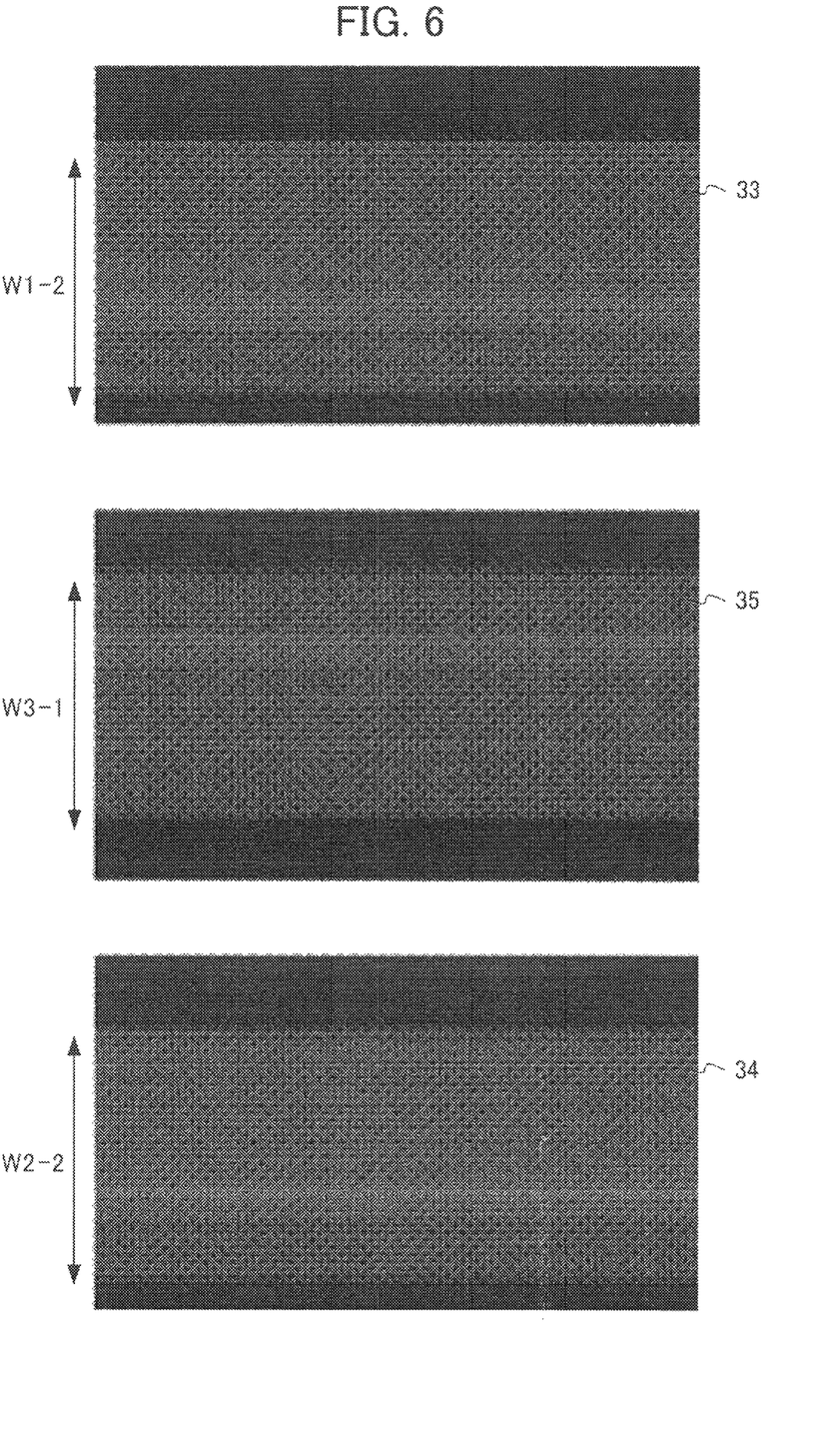
FIG. 6 is an image of a chamfered surface of a semiconductor wafer taken by an imaging device corresponding to the second embodiment.

An image of a chamfered surface of a semiconductor wafer was taken by three imaging devices and images shown in FIG.

6 were obtained. FIG. 6 shows images of a chamfered surface of a semiconductor wafer taken by imaging devices. As shown in FIG. 6, an image 33 is an image of a chamfered surface seen from a main surface side. An image 34 is an image of a chamfered surface seen from a back surface side. An image 35 is an image of a chamfered surface seen to the inside of a semiconductor wafer in a radial direction.

A width W1-2 of the chamfered surface in the image 33 is the width of the chamfered surface seen from the main surface side (a first width). A width W2-2 of the chamfered surface in the image 34 is the width of the chamfered surface seen from the back surface side (a second width). A third width W3-1 of the chamfered surface in the image 35 is the width of the chamfered surface seen to the inside of the semiconductor wafer in a radial direction.

Obtaining the widths W1-2 and W2-2 of the chamfered surface using the images 33 and 34 taken by the imaging devices was thus confirmed to be possible.

Calculation Step and Shape Determination Step

Figure 7:
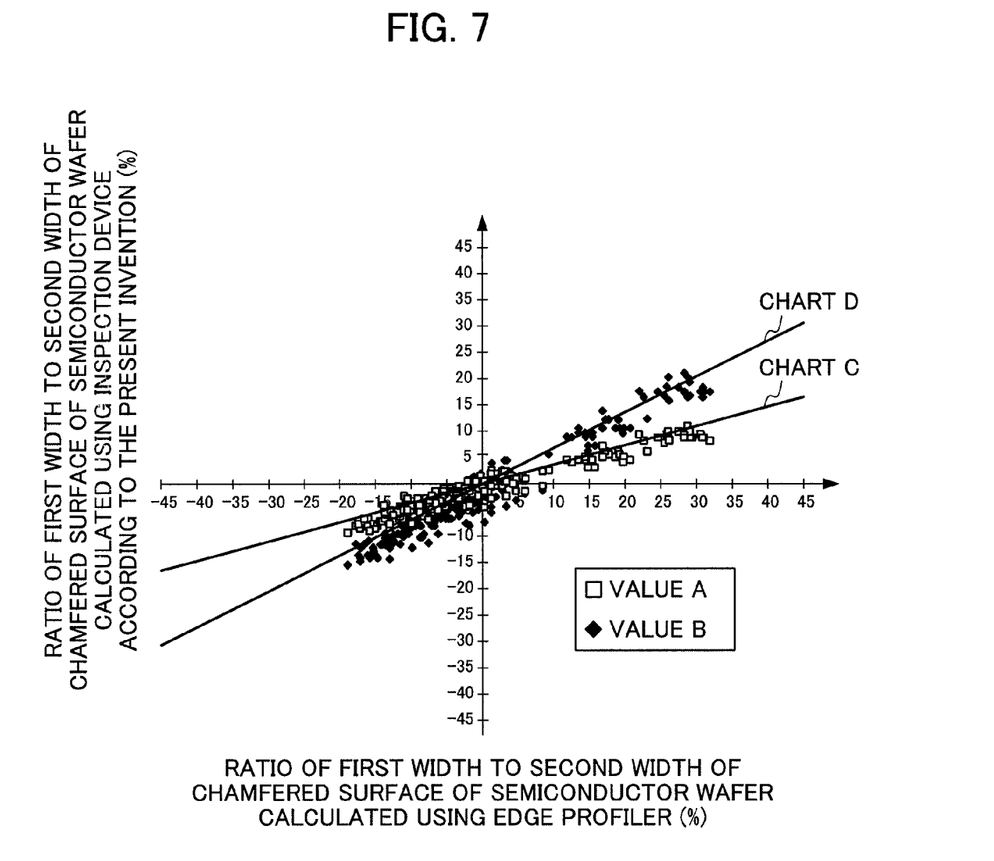
FIG. 7 is a chart showing a correlation between a ratio of a first width to a second width of a chamfered surface calculated using an edge profiler and a ratio of a first width to a second width of a chamfered surface calculated using the inspection device according to the present invention.

FIG. 7 is a chart showing a correlation between a result of obtaining a ratio of a first width to a second width of a chamfered surface calculated using an edge profiler and a result of obtaining a ratio of a first width to a second width of a chamfered surface calculated using the inspection device according to the present invention.

An edge profiler is a device for measuring the shape of a chamfered surface by obtaining images of a chamfered surface seen from a direction of an edge between the edge profiler and the chamfered surface and then analyzing images thus obtained. LEP 1200M manufactured by KOBELCO research institute was used as the edge profiler.

In a chart shown in FIG. 7, a horizontal axis represents a ratio of the first width to the second width of the chamfered surface of the semiconductor wafer, calculated using the edge profiler. A vertical axis represents a ratio of the first width to the second width of the chamfered surface of the semiconductor wafer, calculated using the inspection method of the present invention.

The ratio of the first width to the second width was calculated using the following equation (1).

$$\text{Ratio } P(\%) = ((\text{second width}/\text{first width}) \times 100) - 100 \quad \text{Equation (1)}$$

As shown in FIG. 7, a value A (represented by a white square) is a value obtained by plotting a ratio of a first width to a second width of a chamfered surface calculated using an inspection device β and a ratio of a first width to a second width of a chamfered surface calculated using an edge profiler. On the other hand, a value B (represented by a black diamond) is a value obtained by plotting a ratio of a first width to a second width of a chamfered surface calculated using an inspection device γ and a ratio of a first width to a second width of a chamfered surface calculated using an edge profiler. Here, the inspection devices β and γ have different numbers of imaging devices, and are an inspection device that takes an image of a chamfered surface by two imaging devices (corresponding to the first embodiment) and an inspection device that takes an image of a chamfered surface by three imaging devices (corresponding to the second embodiment), respectively.

In addition, charts C and D are charts showing a correlation between a ratio of a first width to a second width of a chamfered surface calculated using the inspection devices β and γ and a ratio of a first width to a second width of a chamfered surface calculated using an edge profiler.

As shown in FIG. 7, a correlation was found between a result of an edge profiler and a result of the semiconductor wafer inspection method of the present invention, from the charts C and D. Therefore, the semiconductor wafer inspection method of the present invention was confirmed to be capable of accurately determining the shape of a chamfered surface.

What is claimed is:

1. A semiconductor wafer inspection method for inspecting a chamfered surface of a semiconductor wafer including the chamfered surface formed on a main surface, a back surface, and a peripheral portion thereof, comprising:

an imaging step in which a first image is taken using a first imaging device, the first image being an image of the chamfered surface seen from the main surface side and a second image is taken using a second imaging device, the second image being an image of the chamfered surface seen from the back surface side;

a calculation step in which a first width is obtained based on the first image taken in the imaging step, the first width being a width of the chamfered surface seen from the main surface side, a second width is obtained based on the second image taken in the imaging step, the second width being a width of the chamfered surface seen from the back surface side, and a ratio of the first width to the second width thus obtained is calculated;

and a shape determination step in which a form of the chamfered surface is determined to be abnormal in a case where the ratio calculated in the calculation step is out of a predetermined range.

2. The semiconductor wafer inspection method according to claim 1, wherein the first imaging device and the second imaging device are disposed to be line-symmetrical across a plane equally dividing the semiconductor wafer in a thickness direction.

3. The semiconductor wafer inspection method according to claim 1, further comprising a defect detection step in which a defect of the chamfered surface is detected based on the first image and the second image taken in the imaging step.

4. The semiconductor wafer inspection method according to claim 3, wherein, in the imaging step, a third image is further taken using a third imaging device, the third image being an image of the chamfered surface that is seen to the inside of the semiconductor wafer in a radial direction, and, in the defect detection step, a defect of the chamfered surface is detected based on the first image, the second image, and the third image.

* * * * *